United States Patent [19]
Carlsson et al.

[11] Patent Number: 6,020,126
[45] Date of Patent: Feb. 1, 2000

[54] RAPID GENETIC SCREENING METHOD

[75] Inventors: Christina Carlsson, Södertälje, Sweden; Maria T. Dulay, Stanford, Calif.; Mats Jonsson, Gothenberg, Sweden; Peter Nielson, Copenhagen, Denmark; Bengt Nordén, Gothenberg, Sweden; Lap-Chee Tsui, Toronto, Canada; Richard Zare, Stanford, Calif.; Julian Zielinski, Toronto, Canada

[73] Assignees: HSC, Reasearch and Development Limited Partnership, Toronto, Canada; The Board of Trustees of The Leland Stamford Junior University, Palo Alto, Calif.

[21] Appl. No.: 08/821,524

[22] Filed: Mar. 21, 1997

Related U.S. Application Data

[60] Provisional application No. 60/013,913, Mar. 21, 1996, abandoned.

[51] Int. Cl.[7] ............................. C12Q 1/68; C07H 19/00
[52] U.S. Cl. ............................. 435/6; 536/22.1; 204/451
[58] Field of Search ............................. 536/22.1; 435/6; 204/451

[56] References Cited

U.S. PATENT DOCUMENTS 5,593,559  1/1997  Wiktorowicz ........................... 204/453

FOREIGN PATENT DOCUMENTS

WO 92/20703  11/1992  WIPO ............................. C07K 5/00

OTHER PUBLICATIONS

Yonseong et al. "Separation of nucleic acids by capillary electrophoresis in cellulose solutions with mono– and bis–intercalating dyes" Anal. Chem., vol. 66, pp. 1168–1174, 1994.

*Primary Examiner*—Ardin H. Marschel
*Assistant Examiner*—Jezia Riley
*Attorney, Agent, or Firm*—Bozicevic, Field & Francis LLP; Pamela Sherwood

[57] ABSTRACT

A rapid and sensitive detection method capable of reliably distinguishing fragments identical to a defined sequence from fragments containing a single base pair mismatch relative to the defined sequence. The method employs a peptide analog antisense probe, such as a peptide nucleic acid (PNA) probe, which hybridizes with DNA to forms complexes having higher thermal stability, but greater sensitivity to base pair mismatches, than corresponding DNA/DNA complexes. The method may be used in a number of applications, including genetic screening and hybridization sequencing applications.

7 Claims, 4 Drawing Sheets

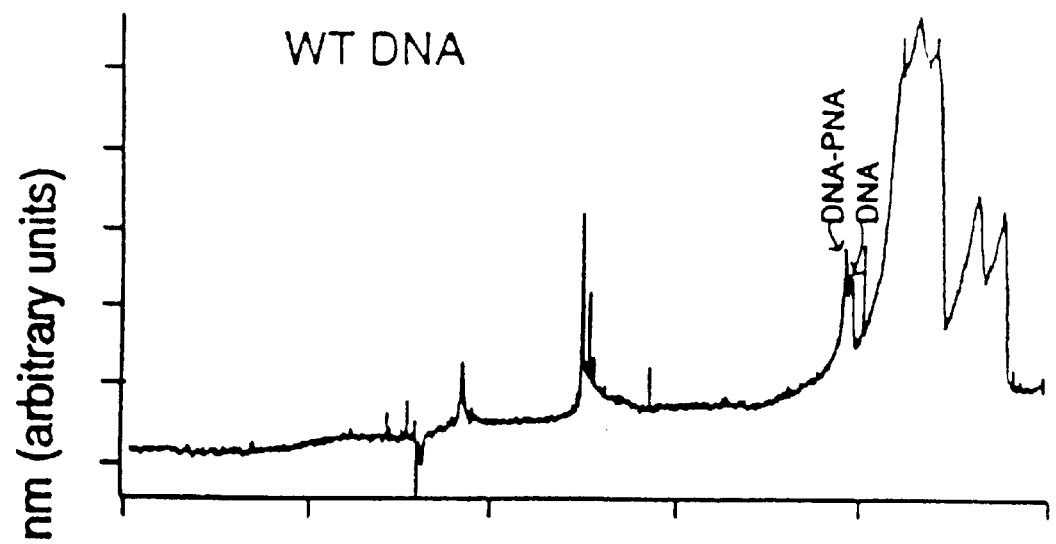
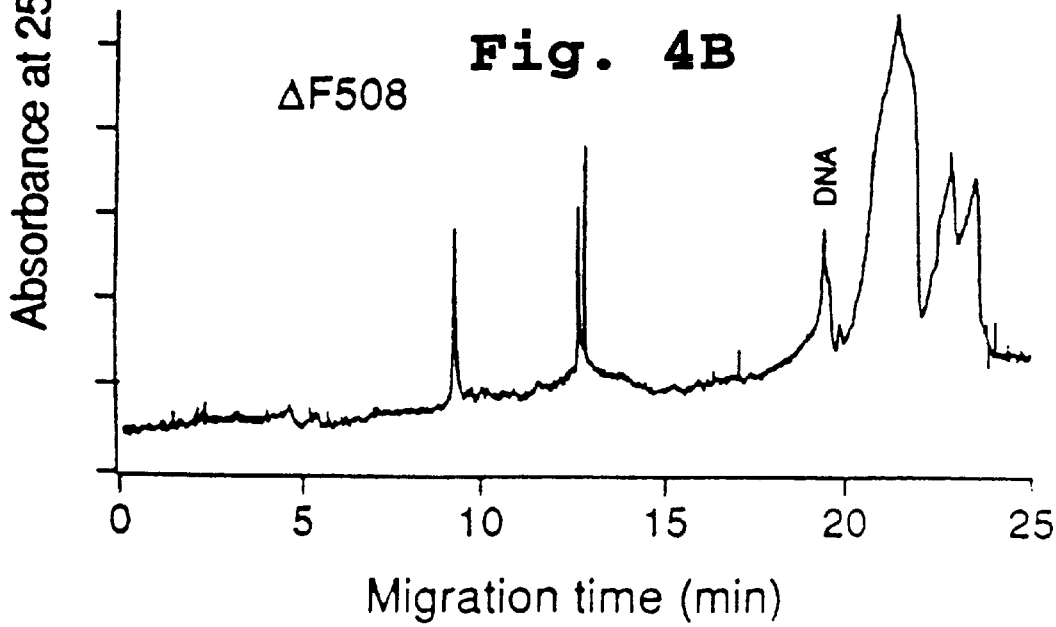

RAPID GENETIC SCREENING METHOD

This application claims priority under 35 U.S.C. 120 to provisional patent application Ser. No. 60/013,913, filed Mar. 21, 1996, incorporated herein by reference.

This work was supported in part by grant number MH 45423-06 awarded by the National Institute of Mental Health. Accordingly, the United States Government has certain rights in this invention.

FIELD OF THE INVENTION

The present invention relates in general to methods of detecting single base-pair mismatches in nucleic acid hybrids formed of a DNA or RNA fragment and a fragment containing nucleotide or nucleoside analogs, such as a peptide nucleic acid (PNA).

REFERENCES

Ausubel, F. M., et al., in CURRENT PROTOCOLS IN MOLECULAR BIOLOGY (John Wiley and Sons, Inc., Media, Pa.) (1988).

Aldridge, et al., Am. J. Hum. Genet. 36:546–564 (1984).

Brock, D. J., in MOLECULAR GENETICS FOR THE CLINICIAN, Cambridge University Press, Cambridge, U.K. (1993).

Chen, et al., Appl. Spectroscopy 42:515–518 (1988).

Chen, et al., Anal. Chem. 61:1590–1593 (1989).

Christensen, et al., Anal. Chem. 61:1344–47 (1989).

Christensen, L., et al., in INNOVATIONS AND PERSPECTIVES IN SOLID PHASE SYNTHESIS AND COMPLEMENTARY TECHNOLOGIES—BIOLOGICAL AND BIOMEDICAL APPLICATIONS—3RD, (Epton, R., Ed.) SPS Oxford Symposia Book, pp. 149–156 (1994).

Cooper, D. N., et al., in THE METABOLIC AND MOLECULAR BASES OF INHERITED DISEASE, (Scriver, C. R., et al., Eds.) McGraw-Hill Inc., New York, Vol. 1, pp. 259–291 (1995).

Cotton, R. G., Mutation Research 285:125 (1993).

Cystic Fibrosis Genetic Analysis Consortium, Human Mutation 4:167 (1994).

Egholm, M., et al., J. Am. Chem. Soc. 114:1895 (1992a).

Egholm, M., et al., J. Am. Chem. Soc. 114:9677 (1992b).

Egholm, M., et al., Nature 365:566 (1993).

Forrest, S., et al., Nature Genetics 10:375 (1995).

Grossman, P. D., and Colburn, J. C., eds., CAPILLARY ELECTROPHORESIS: THEORY AND PRACTICE (Academic Press, Inc., New York) (1992).

Iyer, M., et al., J. Biol. Chem. 270:14712-7 (1995).

Kim, S. K., et al., J. Am. Chem. Soc. 115:6477 (1993).

Merrifield, R. B., J. Am. Chem. Soc. 85:2149–2154 (1963).

Merrifield, B., Science 232:341–47 (1986).

Monnig, C. A., et al., Anal. Chem. 66:280R (1994).

Mullis, K. B., et al., U.S. Pat. No. 4,683,195, issued Jul. 28, 1987.

Mullis, K. B., U.S. Pat. No. 4,683,202, issued Jul. 28, 1987.

Nielsen, P. E., et al., Science 254:1497 (1991).

Noolandi, J., Electrophoresis 14:680 (1993).

Olivera, B. M., et al., Biopolymers 2:245 (1964).

Orum, H., et al., Nucl. Acid Res. 21:5332 (1993).

Summerton, J., et al., U.S. Pat. No. 5,217,866, issued Jun. 8, 1993.

Tabor, S., and Richardson, C. C., Proc. Natl. Acad. Sci. USA 84, 4767 (1987).

Welsh, M. J., et al., in MOLECULAR AND METABOLIC BASIS OF INHERITED DISEASES, (Scriver, C., et al., Eds.) McGraw-Hill, 7th Edition, Chap. 127, pp. 3799–3876 (1994).

Wong, S. S., CHEMISTRY OF PROTEIN CONJUGATION AND CROSS-LINKING, CRC Press, Inc., Boca Raton, Fla. (1991).

BACKGROUND OF THE INVENTION

Many human genetic diseases are caused by only a minor mutation in a specific gene, such as a single-base mismatch (Cooper, et al., 1995). While sequence analysis of these genes provides a direct way of detecting genetic aberrations, it is at present too time consuming and expensive to be practical in broad-based diagnostic applications. The present invention provides a simple method for reliably, inexpensively and rapidly analyzing sequence alterations as minor as single base-pair mismatches in polynucleotide fragments derived from genes whose sequences are altered in a genetic disease.

SUMMARY OF THE INVENTION

In one aspect, the present invention includes a method of detecting, in a sample, containing a mixture of polynucleotides, a target polynucleotide region having a sequence identical to a defined sequence. The method includes (i) reacting the sample with a polynucleotide analog antisense probe (PAAP), having a sequence complementary to the defined sequence, under conditions that allow the formation of a complex between perfectly matched PAAP and target-region sequences, but not between imperfectly matched PAAP and target-region sequences, (ii) separating the complexed from non-complexed polynucleotides in the sample, and (iii) detecting the presence of the complex. In one embodiment, the PAAP is a peptide nucleic acid (PNA). The target polynucleotide region may be contained in a double-stranded polynucleotide or in a single-stranded polynucleotide. The reacting may include contacting the sample with the PAAP at about room temperature, and subsequently elevating the temperature of the reaction to achieve conditions that allow the formation of complexes between perfectly matched PAAP and target-region sequences, but not between imperfectly matched PAAP and target-region sequences. In one embodiment, the method is used in distinguishing the target nucleotide region from a second target nucleotide region having single base pair mismatch with respect to the defined sequence, wherein the reacting is carried out at a temperature between about 50° C. and about 80° C.

In a general embodiment, the PAAP is immobilized on a solid support, the reacting includes incubating the sample with the support, the separating includes washing the support to remove unbound polynucleotides, and the detecting includes detecting support-bound polynucleotides. The detecting may include adding labeled polycationic reporter or ethidium bromide. Alternatively, the detecting may include using a reporter moiety attached to a polynucleotide, containing the target polynucleotide region, such as a fluorescent moiety.

In another general embodiment, the detecting includes detecting using capillary electrophoresis instrument, such as a free-solution capillary electrophoresis instrument. The PAAP may include a reporter moiety, such as a fluorescent moiety.

These and other objects and features of the invention will become more fully apparent when the following detailed description is read in conjunction with the accompanying drawings.

BRIEF DESCRIPTION OF THE FIGURES

(FIG. 2A), 50° C. (FIG. 2B), and 70° C. (FIG. 2C).

FIGS. 4A and 4B show a comparison of electropherograms at 50° C. of CF wild-type double-stranded (ds) gene fragment (SEQ ID NO:8) hybridized with PNA probe (SEQ ID NO:1) (FIG. 4A) and ΔF508 mutant ds gene fragment (SEQ ID NO:9) hybridized with PNA probe (FIG. 4B).

DETAILED DESCRIPTION OF THE INVENTION

I. Definitions

Figure 1A:
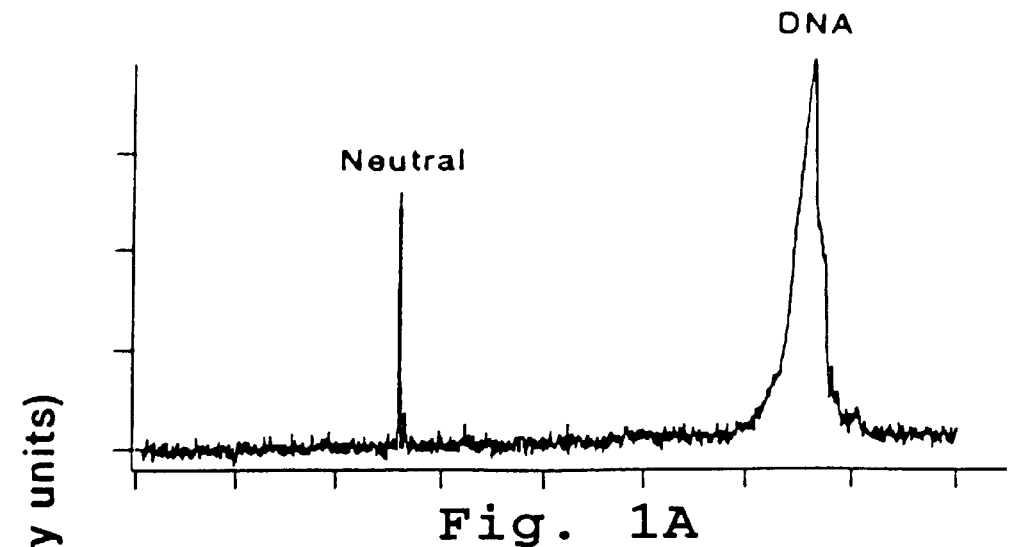
FIGS. 1A, 1B and 1C show free-solution electropherograms of a 50-mer single-stranded cystic fibrosis (CF) wild-type DNA (SEQ ID NO:2) at 50° C. in the absence of PNA probe (FIG. 1A), following addition of 1 μl PNA probe (SEQ ID NO:1) (FIG. 1B), and following addition of 1.4 μl PNA probe (FIG. 1C). Absorption detection was at 254 nm.

A polynucleotide sequence or fragment is "derived from" another polynucleotide sequence or fragment when it contains the same sequence of nucleotides as are present in the sequence or fragment from which it is derived. A polynucleotide or polynucleotide fragment may consist of deoxyribonucleic acid (DNA), ribonucleic acid (RNA), or nucleotide or nucleoside analogs (e.g., peptide nucleic acids; PNA).

A "polynucleotide analog antisense probe" (PAAP) refers to a fragment that (i) is comprised of nucleotide analogs or nucleoside analogs, (ii) is capable of hybridizing to single stranded or double-stranded DNA in a base-specific manner, and (iii) is capable of imparting charge or mass characteristics on PAAP/DNA complexes that can distinguish such complexes from DNA/DNA complexes. PAAPs for use in genetic screening applications have sequences that are the reverse complement of the different variants derived from a mutation-containing region of a gene of interest. The sequence of such a PAAP can correspond to the sequence of a wild-type gene or to the sequence of any of the mutant genes.

A first single-stranded polynucleotide fragment hybridizes in a "base-specific manner" to a second single-stranded polynucleotide fragment if the sequence of the second fragment is similar or identical to the reverse complement of the sequence of the first fragment over a defined region and the fragments can form hybrids under standard hybridization conditions.

A single-stranded polynucleotide fragment hybridizes in a "base-specific manner" to a double-stranded polynucleotide fragment if the sequence of one of the strands of the double-stranded fragment is similar or identical to the reverse complement of the sequence of single-stranded fragment over a defined region and the fragment can form a complex with the double-stranded fragment.

"Imperfectly matched" or "mismatched" sequences are sequences that are not reverse-complements of one another over a defined region. The change of a single basepair in one of two sequences that would otherwise be reverse-complements of one another results in imperfectly matched or mismatched sequences.

"Perfectly matched" sequences are sequences that are reverse-complements of one another over a defined region. "Perfectly matched" fragments are fragments that have mo mismatches or gaps in their basepairing over a defined region.

A "complex" with respect to PAAP and polynucleotide fragments refers to (i) a duplex containing a PAAP hybridized to a corresponding polynucleotide fragment, or (ii) a triplex formed either of two PAAPs and a target polynucleotide region of a selected gene, or one PAAP and a target polynucleotide region in a double-stranded polynucleotide fragment.

II. Overview of the Invention

Methods of the present invention employ a polynucleotide analog antisense probe (PAAP), such as a PNA probe, directed to a region of a gene whose sequence is altered in a genetic disease, where that region is a "hot spot" for mutations—i.e., contains many of the mutations giving rise to the disease. The characteristics of the probe are such that, in a selected temperature range, it forms sequence-specific complexes with a polynucleotide containing the target region only if there is a perfect match in base pairing between the probe and the target region. If there is even a single base-pair mismatch between the probe and the target region, the probe and the polynucleotide containing the test region do not form a complex in the selected temperature range.

An exemplary technique for the detection of such complexes is free-solution capillary electrophoresis (FSCE), which, when performed using a modified instrument (see below), can maintain temperatures in the selected temperature range, i.e., high enough to maintain prevent reannealing of mismatched hybrids (e.g., 50–95° C., preferably 50–80° C.). Another exemplary detection method employs PAAP fragments immobilized on a solid support (e.g., a strip or a planar array), where the support containing the PAAPs is contacted with a test sample containing polynucleotides, and regions of the support containing duplexes of a PAAP (e.g., PNA) and a polynucleotide from the test sample are detected using a reporter capable of detecting duplexes.

As detailed herein, methods of the present invention may be employed for the detection of simple mutations causing genetic diseases, including single-base substitutions. Examples 1 and 2 demonstrate that a 15-mer peptide nucleic acid (PNA) probe can distinguish normal and mutant sequences in both single-stranded and double-stranded DNA fragments from the cystic fibrosis gene. A second exemplary application of the methods of the present invention is in hybridization-based sequencing.

III. Antisense Probes

Polynucleotide analog antisense probes (PAAPs) preferably have the following characteristics: (i) PAAP/DNA duplexes have a higher thermal stability than DNA/DNA duplexes, (ii) PAAP/DNA duplexes are more sensitive to single base pair mismatches than DNA/DNA duplexes, and (iii) PAAP/DNA duplexes form at a faster rate than DNA/DNA duplexes.

Furthermore, PAAPs preferably have a neutral or positively-charged backbone, which helps to confer the above characteristics and results in PAAP/DNA complexes with a different charge/mass ratio than DNA/DNA complexes.

A. PNA Oligomers

Peptide Nucleic Acid (PNA) oligomers are exemplary PAAPs. PNA is a DNA analog, or mimic, in which the backbone is structurally homeomorphous with the deoxyribose backbone and consists of N-(2-aminoethyl)glycine units to which the nucleobases are attached (Nielsen, et al., 1991; Egholm, et al., 1992a; Egholm, et al., 1992b; Egholm, et al., 1993). PNA differs from DNA in that the negatively-charged ribose-phosphate backbone of the latter is replaced by its neutral peptide counterpart, in this case glycine. By choosing the sequence of the four bases in PNA to be complementary to one of the stands of DNA, the PNA probe hybridizes by Watson-Crick pairing. Moreover, PNA complexes with double-stranded DNA in a base-specific manner.

PNA probes have a number of advantages over DNA probes. First, PNA probes form more stable hybrids with perfect-match complementary DNA or RNA fragments than do corresponding DNA or RNA probes. This stronger binding is attributed in large part to the lack of electrostatic repulsion between the PNA and DNA strands. It is estimated that PNA/DNA duplexes are generally 1° C. per base pair more stable thermally than corresponding DNA/DNA duplexes (Egholm, et al., 1993). Accordingly, whereas a given 15-mer DNA/DNA duplex may have a $T_m$ of 55° C., the corresponding PNA/DNA duplex may have a $T_m$ of about 70° C. This characteristic can be used to reduce the background in hybridization experiments by washing the samples at a temperature high enough to melt DNA/DNA hybrids (even if they are a perfect match) but low enough to maintain integrity of the more stable perfectly matched PNA/DNA hybrids.

Second, due to the neutral PNA backbone, the $T_m$s of PNA/DNA duplexes are largely independent of salt concentration and their hybridization does not require $Mg^{++}$. These characteristic may be exploited in designing hybridization conditions which disfavor the formation of DNA/DNA duplexes (which have $T_m$s that are highly dependent on ionic strength and require $Mg^{++}$).

Third, base pair mismatch discrimination is greater for PNA/DNA than for the corresponding DNA/DNA duplexes (Orum, et al., 1993). In other words, a PNA/DNA mismatch is more destabilizing than a mismatch in a DNA/DNA duplex. A single mismatch in mixed PNA/DNA 15-mers lowers the $T_m$s by 8–20° C. (15° C. on average), while a single mismatch in corresponding DNA/DNA duplexes lowers the $T_m$s by 4–16° C. (11° C. on average). The effect is a wider temperature range in which perfectly-matched PNA/DNA duplexes are maintained and duplexes containing mismatches are not.

Fourth, PNA hybridizes with DNA faster than DNA hybridizes with DNA (Iyer, et al., 1995), due primarily to the fact that PNA is neutral, and is thus not repelled by electrostatic forces (as is the case for two negatively-charged DNA fragments hybridizing with one another). This enables a more rapid analysis of samples by reducing the time required for the hybridization reaction.

Fifth, PNA oligomers can typically bind in a base-specific manner to a double-stranded DNA molecule. In the case of PNA oligomers containing only thymine and cytosine, the binding probably occurs by displacing one of the DNA strands into a "D-loop" and forming a PNA/DNA/PNA triplex. Regardless of the mechanism by which PNA binds to dsDNA, however, the binding may be exploited to detect mutations in a sample containing non-denatured dsDNA fragments.

Sixth, due to the greater stability of PNA/DNA duplexes relative to DNA/DNA duplexes, shorter PNA probes (as short as ~10 bp) may be used to specifically bind to DNA. In cases where the test sample DNA contains only amplified products from a particular locus (i.e., the complexity of the sequences in the sample is vastly-reduced relative to total genomic DNA), such short PNA probes are capable of providing excellent selectivity and sensitivity.

PNA fragments preferably associate with DNA fragments in an antiparallel configuration, that is with the amino terminal of the PNA facing the 3' end of the oligonucleotide (Egholm, et al., 1993). The PNA sequences provided herein are presented with the N-terminus at the left of the sequence and the C-terminus at the right of the sequence. Accordingly, the sequence of PNA probes used according to the methods of the present invention is preferably designed such that hybrids are formed when the PNA associates in an antiparallel configuration. It will be understood, however, that stable PNA/DNA hybrids may also form with the PNA and DNA associated in a parallel configuration (Egholm, et al., 1993). Such parallel hybrids typically have a lower melting temperature (Tm), but this feature may be exploited in applications requiring such a lower Tm.

Further, as was mentioned above, PNA may also form hybrids with RNA fragments, and teachings herein referring to PNA/DNA hybrids are understood to apply to PNA/RNA hybrids where such PNA/RNA hybrids may be reasonably employed in the particular application being discussed. The melting temperatures for PNA/RNA hybrids are similar to those for PNA/DNA hybrids, with the antiparallel configuration in PNA/RNA hybrids also being more stable that the parallel configuration.

Examples 1 and 2 illustrate the utility of PNA probes in the methods of the present invention. Example 1 demonstrates that PNA probes can be used to distinguish single-stranded (ss) DNA fragments having a perfect match from ssDNA fragments having even a single base-pair mismatch with the probe. The Example also shows the effects of temperature on the hybridization and detection characteristics.

Example 2 shows that PNA probes can bind to double-stranded DNA with no loss of discriminatory activity. The dsDNA was polymerase chain reaction (PCR)-amplified from human genomic DNA isolated from an individual with the ΔF508 CF mutation and an individual with two copies of a normal cystic fibrosis transmembrane conductance regulator (CFTR) gene.

IV. PNA Probe Synthesis

As described below, PNA probes are synthesized using modified solid phase peptide synthesis protocols (e.g., the protocol described by Egholm, et al., 1992a,b). Additional protocols may be obtained from PerSeptive Biosystems. In these protocols, monomers or salts are typically dissolved in N,N'-dimethylformamide (DMF) or N-methylpyrrolidone (NMP) and coupled to the growing chain with a uronium salt activator such as O-(7-azabenzotriazol-1-yl)-1,1,3,3-tetramethyluronium hexafluorophosphate (HATU). After synthesis, removal of protecting groups and cleavage of the oligomer from the resin may be achieved with, e.g., trifluoromethanesulfonic acid (TFMSA). If required, the crude PNA oligomer can then be further purified by reversed-phase HPLC.

A polyethylene glycolpolystyrene support (PEG-PS; available from PerSeptive Biosystems) is preferred for use with PNA synthesis reactions. This support can provide significantly higher quality PNAs than standard 4-methylbenzhydrylamine (MBHA)-type resins. The PEG-PS resin is derivatized with a benzhydrylamine-based linker for synthesis of C-terminal amidated PNAs. The use of the PEG-PS support improves stepwise coupling yields because the PEG spacer essentially solvates the growing PNA chain, and thus facilitates rapid acylation of the N-terminal amino group.

V. Sample Preparation

Polynucleotide-containing samples suitable for use with the present invention are obtained from appropriate sources. For example, samples for genetic screening applications are typically derived from genomic DNA, which may be isolated from nucleated blood cells of test subjects using known techniques (e.g., Aldridge, et al., 1984). Commercial kits for the isolation of genomic DNA are also available (e.g., "PUREGENE" DNA Isolation Kit, Gentra Systems, Inc., Minneapolis, Minn.).

The isolated DNA may then be used directly and/or it may be used as a template for amplification (e.g., using PCR). If the isolated DNA is used in the methods of the invention without amplification, it is preferably digested, using one or more restriction endonucleases, into fragments having selected size distributions (e.g., Ausubel, et al., 1988). The range of the size distribution depends on the detection method. For example, if FSCE is used in the detection step, the fragments are preferably on the order of few hundred bp in length or less, such that a polynucleotide analog antisense probe (e.g., PNA) can introduce an asymmetry into the PAAP/DNA hybrid. The greatest degree of asymmetry will be introduced when the PAAP fragment and the test polynucleotide fragments are about the same length.

Alternatively, the isolated DNA may be amplified, e.g., using PCR, prior to being assayed by the methods of the present invention as illustrated in Example 2. For example, in a genetic screen for possible mutations in a selected gene or locus, exon(s) containing potential mutations are amplified by PCR and the amplification products are used as the polynucleotide-containing test sample in the methods of the invention. Amplifying the DNA prior to analysis has the added advantage of providing a set of polynucleotide fragments having an essentially uniform size.

VI. Hybridization/Complex Formation

Polynucleotide antisense probes employed in the practice of the present invention preferably hybridize to sample DNA fragments faster, and result in more stable hybrids, than corresponding DNA probes. Probes having these characteristics (e.g., PNA probes) may be hybridized with sample DNA in any of several ways. For example, dsDNA may be denatured by heating to ~95° C. in the presence of a molar excess of PAAPs, allowed to cool to a temperature at which PAAPs can anneal to corresponding sample DNA sequences, but at which stable DNA/DNA hybrids will not form, and then put on ice. Double-stranded fragments in the sample may then be detected as described below, e.g., by employing a detection reagent or reporter that selectively identifies double-stranded DNA.

Alternatively, in the case of PAAPs such as PNAs that bind to dsDNA at room temperature, the PAAP may simply be incubated with a sample containing dsDNA at room temperature (e.g., as in Example 2), and the sample can be analyzed under conditions (e.g., elevated temperature) where perfectly-matched PAAP/DNA complexes are maintained, but DNA/DNA hybrids and imperfectly-matched PAAP/DNA complexes are not (see below).

An important aspect of the present invention is the use of temperature to discriminate between PAAP/DNA complexes containing mutations as minor as a single basepair mismatch from perfectly-matched complexes. It will be understood that the precise temperature range in which perfectly-matched hybrids are maintained, but in which mismatches are not, will typically need to be determined empirically according to the guidance presented herein. For example, to determine such a range for a set of PAAPs designed to detect known mutations in a selected gene, the PAAPs are tested using DNA amplified from all possible mutant and wild-type templates. A temperature range that results in the maintenance of all perfectly-matched hybrids and no mismatched hybrids is then empirically-identified using, for example, test runs on capillary electrophoresis apparatus such as described below in Example 1.

VII. Detection of Complexes

A. Capillary Electrophoresis

Capillary electrophoresis (CE) provides a convenient method for the analysis of PAAP/DNA hybrids of the present invention. A number of review articles and books provide an introduction to principles and applications of capillary electrophoresis (Monnig, et al., 1994, Grossman and Colburn, 1992, Christensen, et al., 1989, Chen, et al., 1988, 1989). Although a variety of different CE formats may be employed (e.g., capillary zone electrophoresis, capillary gel electrophoresis, micellar electrokinetic capillary electrochromatography, capillary isoelectric focusing, and capillary isotachophoresis, as well as variations of micro liquid chromatography), the methods of the invention are particularly amenable to analysis using free-solution capillary electrophoresis (FSCE).

At first glance, FSCE appears to be an unlikely candidate for such a rapid detection method, since it is known that the electrophoretic mobility of freely draining polyelectrolyte coils is nearly independent of molecular weight (because the electrical driving force and the frictional force are both proportional to the length (Olivera, et al., 1964)).

However, experiments performed in support of the present invention suggest that this scaling symmetry between electrical and frictional forces may be broken for molecules in which asymmetries are created, either by changing the charge or mass distribution, or because of hydrodynamic effects. According to the present invention, such an asymmetry is created by the association of a DNA fragment with an antisense fragment (e.g., PNA) having a different net charge from that of the DNA fragment. In the case of PNA/DNA hybrids, this symmetry breaking is achieved by the fact that the backbone of PNA is non-ionic (Noolandi, 1993). Hence, the hybridization of a PNA fragment to a DNA fragment does not change the total charge of the resulting hybrid fragment (relative to the charge of the DNA alone) but strongly impacts its hydrodynamic properties as shown by flow linear dichroism measurements (Kim, et al., 1993).

Accordingly, methods of the present invention utilizing FSCE preferably employ PAAPs that impart an asymmetry (e.g., mass/charge asymmetry) on the resulting hybrid (relative to a DNA/DNA hybrid). As is exemplified below, such "asymmetric" hybridization products can be readily separated by free-solution capillary electrophoresis. Another variation of capillary electrophoresis having similar temperature and separation characteristics is capillary electrochromatography.

B. Detection on Solid Supports

Another method of detecting PAAP/DNA hybrids is by immobilizing either the PAAPs or the DNA on a solid support, contacting the support with the corresponding oligomer under conditions which allow the maintenance of probe/target hybrids between perfectly matched sequences, but not between mismatched sequences, washing off unbound oligomer, and detecting bound oligomer. In a preferred embodiment, the PAAP (e.g., PNA) is immobilized on the solid support, a sample containing DNA fragments to be tested is contacted with the immobilized PAAP, and bound DNA is detected using a reporter that labels or identifies PAAP/DNA complexes.

PAAPs such as PNAs may be immobilized on a suitable solid support using known techniques (e.g., Wong, 1991; Summerton, et al., 1993). For example, the PNA may be reacted with a suitable crosslinking agent, such as disuccinimidyl suberate, and added to the support material, such as latex microparticles containing suitable linker arms terminating in primary amine moieties.

Suitable solid supports include agarose, cellulose, nitrocellulose, latex, polystyrene, and other commercially available strip or particle-bead support material having surface-reactive or activatable groups which allow efficient coupling of polymer molecules, particularly through polymer-bound spacer arms.

The solid support is preferably one that may be formed into a planar substrate suitable for the manufacture of test strips, dip-sticks and planar arrays of immobilized PAAPs. Such supports include membranes (e.g., nitrocellulose, nylon, or polyvinylidene difluoride (PVDF) membranes) as well as soluble polymers dissolved in a solvent.

Membrane supports may be activated with suitable coupling or modifying agents to enable the covalent binding of a PAAP, such as a PNA, to the membrane. Examples of suitable coupling, modifying and crosslinking agents are well known (e.g., Wong, 1991). Alternatively, some membranes (e.g., nylon or nitrocellulose) may be used as solid supports without any chemical modification. An aliquot of a solution containing a PAAP is dispensed onto the membrane and preferably drawn through the membrane by, e.g., vacuum filtration. The PAAP binds to the membrane via electrostatic interactions. These interactions may be optionally stabilized by cross-linking (e.g., UV crosslinking).

The membrane containing the immobilized PAAP is then reacted with a sample containing target polynucleotides under conditions that allow the formation of a complex between perfectly matched PAAP and target-region sequences, but not between imperfectly matched PAAP and target-region sequences (see discussion above). Following such a reaction, the membrane is washed to separate complexed from non-complexed polynucleotides, and PAAP/target complexes are detected using a reporter, such as ethidium bromide. It will of course be understood that in alternative embodiments, a population of polynucleotides containing target polynucleotides, rather than PAAPs, may be immobilized on the solid support, and probed with a solution containing PAAPs. The support is then washed and complexes between target polynucleotides and PAAPs are detected.

Another approach to producing a planar substrate containing regions having immobilized PAAPs is to dissolve a suitable soluble polymer (e.g., cellulose or polyvinyl) in a solvent, preferably a mild non-aqueous solvent (e.g., ethanol, methanol) that does not adversely affect the PAAP, reacting the solution with a PAAP (using standard chemical protocols developed for immobilization of polynucleotides and polypeptides to solid supports; see, e.g., Wong, 1991) and depositing aliquots of the solution onto a flat surface from which the solvent can evaporate. This generates a film of the polymer containing immobilized PAAP on the flat surface. The polymer may be applied at discrete regions to a flat carrier substrate (e.g., a piece of filter paper, plastic strip, etc.) to generate an array of PAAPs, each having a different sequence. This array may then be contacted with a polynucleotide-containing sample derived from a test subject at a selected hybridization temperature which allows the maintenance of perfectly-matched hybrids, but not mismatched hybrids, and the perfectly-matched hybrids may be detected using a reporter.

C. Reporter Moieties/Labels

PAAP/DNA hybrids may be detected using a reporter that (i) is either attached to the PAAP or to the sample DNA fragments, or (ii) labels formed PAAP/DNA complexes. In cases where the PAAP is immobilized on a solid support, the reporter moiety is typically either attached or incorporated in the test DNA fragments, or is designed to bind to PAAP/DNA complexes once they have formed. For example, a reporter may be incorporated into a PCR reaction used to amplify, from total genomic DNA, the exon(s) of the gene being examined. The reporter may be attached to one or both primers used in the PCR reaction (e.g., biotinylated primer), or it may be incorporated during the PCR reaction.

In applications where the PAAP is not immobilized, the reporter may be attached or incorporated in to the PAAP fragment itself. For example, it is possible to modify a PNA oligomer during synthesis with amino acids and various reporters, such as fluorescein, biotin or rhodamine. When one of these reporters is incorporated, however, it is generally necessary to have a linker between the PNA strand and the reporter. A preferred linker is [2-(NBoc-2-aminoethoxy)ethoxy]aceffc acid (Boc-AEEA-OH), which can be coupled using standard protocols. Furthermore, PNA fragments having a customer-specified sequence and labeled with a reporter (e.g., a fluorescent label such as fluorescein or rhodamine, or other labels such as biotin) may be purchased from PerSeptive Biosystems (Framingham, Mass.).

Alternatively, in applications where perfectly-matched PAAP/DNA hybrids comprise essentially the only duplex or triplex polynucleotides in the sample (e.g., a test strip with immobilized PAAP fragments following hybridization with test sample DNA and washing), a probe that selectively labels or identifies duplex or triplex polynucleotides may be employed (e.g., ethidium bromide). Further, in applications where essentially the only negatively-charged species are DNA molecules bound to PAAP fragments, a probe that selectively binds to negatively-charged polymers, such as a polycationic reporter (Summerton, et al., 1993), may be employed.

VIII. Applications

A. Genetic Diagnostics

An important application of the present invention is in the area of genetic diagnostics. As is discussed below, the methods of the present invention may be used to screen for any of a variety of genetic diseases whose genetic defect is known, particularly if the genetic defect consists of localized mutations (e.g., point mutations, triplet insertions/deletions, etc.) rather than large alterations (e.g., deletions of a large portions of the gene). Example of such genetic diseases include sickle-cell disease, Duchenne muscular dystrophy, cystic fibrosis and Tay Sachs. Such disease may be diagnosed using the guidance herein in combination with techniques known in the art.

The methods disclosed herein may be readily adapted to automated genetic testing of a large number of samples simultaneously. For example, the methods may be used with fluorescent PNA probe libraries with multiple fluorescent tags for multiplex testing of one or more exons in screening strategies for any genetic disease with a known spectrum of mutations (Forrest, et al., 1995). In one embodiment, PNA probes corresponding to wild-type sequence(s) and known mutant sequence(s) are each labelled with a different fluorescent label, hybridized with sample DNA containing fragments of the gene region to be analyzed, and analyzed. The signal from the detector (e.g., UV-absorbance detector in a CE instrument; see Example 1) is used to detect the presence of double-stranded polynucleotide fragments, and the position of this signal is compared to a fluorescence signal of the resolved sample. The identity of the PNA probe associated with the ds fragment peak is determined from the nature of the fluorescence signal. The fluorescence of the resolved sample may be measured as the sample exits the CE instrument or inside the CE instrument.

In another embodiment, a PAAP library formed of PAAP probes having different sequences (e.g., wild-type and mutant sequences) is arranged in a spatially-addressable manner on a solid support. If there is only a limited number (e.g., <10) of possible sequences which cover essentially all known sequences at the locus for which the test is designed, then the solid support may take the form of a strip ("dip stick"), with horizontal bands along the strip containing immobilized PAAP fragments, with different bands having PAAP fragments with different sequences. Alternatively, if there is a large number of sequences to be assayed, the solid support may take the form of a planar array of regions, with the different regions containing PAAP fragments having different sequences. The sample containing polynucleotides with target regions is then reacted with the support under conditions allowing the formation of complexes between the bound PAAPs and corresponding polynucleotides from the sample, uncomplexed polynucleotides are washed off at a temperature that allows maintenance of complexes between perfectly-matched PAAP/DNA complexes, but not imperfectly-matched complexes, and bound complexes are detected.

One of the characteristics that is desirable in any screening method is the ability to distinguish between the three possible genotypes: (1) the wild-type homozygote (wt/wt) (2) the mutant homozygote (m/m), and (3) the heterozygote (wt/m) (Brock, 1993). These three genotypes may be distinguished using the methods of the present invention. For example, in a CE-based screen employing PNA probes labelled with different fluorescent probes for wild-type and mutant alleles, wild-type homozygote can be detected as a single peak coincident with the wild-type fluorescence signal, mutant homozygotes can be detected as a single peak coincident with the mutant fluorescence signal, and heterozygotes can be detected as two smaller peaks, one coincident with the wild type fluorescence signal and the other coincident with the mutant fluorescence signal.

Similarly, in a solid support-based detection scheme, wild-type homozygotes can be detected as a positive hybridization or complex-formation signal at the "wild-type" location in the array, with no positive signal at any of the "mutant" locations, mutant homozygotes can be similarly detected as a positive signal at one (possibly two, if the two copies of their genes have two different mutations) "mutant" location, and heterozygotes can be detected as a positive signal at the "wild type" and at one "mutant" location.

B. Sequence Analyses

The approaches detailed above may also be applied to determine the sequence of a selected DNA fragment by hybridization sequencing. Current approaches to hybridization sequencing suffer from the drawback that it is virtually impossible to identify a single set of conditions (i.e., salt concentration, temperature, etc.) that will result in the maintenance of perfectly-matched DNA/DNA hybrids but not DNA/DNA hybrids containing a single mismatch for all the possible hybrids contained on a particular array.

According to experiments performed in support of the present invention, however, PAAPs, e.g., PNAs, may be used in hybridization sequencing applications to overcome this problem. In particular, due to the wider temperature range in which perfectly-matched PNA/DNA complexes remain associated and imperfectly-matched complexes do not, the invention contemplates the construction of arrays of discrete regions, each region containing PNAs having one of a plurality of sequences represented on the array, where the entire array could be reacted under conditions (in particular, at a temperature) that permit perfectly-matched PNA/DNA complexes to remain associated and imperfectly-matched complexes to dissociate. This aspect of the invention may be practiced using, e.g., a planar array or set of arrays containing PAAPs (e.g., PNAs) of a selected length (e.g., 8-mer or 10-mer), where each position on an array contains a PAAP with a single sequence, and the PAAPs represented in the set of arrays collectively represent all possible permutations of sequences of oligomers of the selected length. The array or set of arrays is contacted with the target fragment to be sequenced under conditions (e.g., temperature conditions) that allow the maintenance of PAAP/target hybrids between perfectly matched sequences, but not between mismatched sequences. Bound target fragments are detected, e.g., as described above, and the sequence is determined from the sequences of PAAPs that formed hybrids with the target fragment using standard computational approaches.

IX. Advantages of the Invention

Methods of the present invention enable extremely rapid genetic screening, since the total analysis times (hybridization and detection) are extremely fast—on the order of 15–20 minutes. This analysis time is significantly less than is required by other mutation analysis approaches, which typically employ the polymerase chain reaction (PCR; Mullis, 1987; Mullis, et al., 1987) as a step in the analysis (Cotton, 1993).

Furthermore, methods of the present invention employing FSCE as the detection method do not require the preparation of separation matrices, making them simpler, cheaper and faster than methods that do require such matrixes. Also, because PNA/DNA complexes have a higher denaturation temperature than DNA/DNA hybrids, the experiments can be carried out at elevated temperatures where stable DNA—DNA hairpin structures, responsible for band compressions in gel electrophoresis (Tabor and Richardson, 1987), are eliminated. In addition, methods of the present invention may be applied in ways that do not require the use of enzymes, such as Taq polymerase, or other costly reagents, such as dNTPs, which are required in PCR-based diagnostic methods.

The following examples illustrate but in no way are intended to limit the present invention.

MATERIALS AND METHODS

A. Buffers

Running Buffer (50 mM TBE) 50 mM tris (hydroxymethyl)aminomethane 50 mM boric acid 1.25 mM ethylenediaminetetraacetic acid (EDTA)

B. Synthesis of PNA

PNA probes were synthesized using a modification of Merrifield synthesis (Merrifield, 1963, 1986) as previously described (Egholm, et al., 1992a,b). Briefly, benzyloxycarbonyl (Z) (Boc/Z) -protected monomers were assembled using optimized solid phase technology (Christensen, et al., 1994) on a PerSeptive Biosystems (Framingham, Mass.) "EXPEDITE" instrument. Deprotection and release of the free PNA were done with anhydrous HF under standard conditions. PNA oligomers, as well as additional PNA probe synthesis protocols, may be ordered from PerSeptive Biosystems.

C. Modified FSCE Instrument

A P/ACE Model 2000 (Beckman Instruments, Fullerton, Calif.) capillary electrophoresis instrument was modified as follows to enable the running of experiments above 50° C. The instrument was equipped with a 67-cm long×75-mm inner diameter (effective length of 60 cm) fused-silica capillary from Polymicro Technologies, Inc. (Phoenix, Ariz., USA), enclosed in the capillary cartridge provided with the instrument.

In an unmodified P/ACE Model 2000 capillary electrophoresis instrument, a fluorocarbon coolant contained in a coolant reservoir is circulated, via a recirculating pump, through the cartridge to keep the capillary at a constant selected temperature.

In the modified instrument used in the present experiments, the coolant reservoir was removed from the instrument and placed in a water bath set to the desired temperature (typically between about 50° C. and about 70° C.). In addition, the standard temperature controller computer chip was replaced with a high-temperature controller chip (obtained from Beckman Instruments, Fullerton, Calif.), which enabled programming of the instrument to run at temperatures above 50° C.

EXAMPLE 1

Detection of Mismatches in Single-stranded CFTR DNA Fragments

A 15-mer PNA (SEQ ID NO:1) complementary to a DNA segment corresponding to the location of the most common mutation (ΔF508) of the cystic fibrosis transmembrane conductance regulator (CFTR) gene (Welsh, et al., 1994) was synthesized as described above. The ΔF508 mutant accounts for approximately two thirds of known CF mutations, the exact percentage varying with different populations (Cystic Fibrosis Genetic Analysis Consortium, 1994). This probe was tested against 4 test sequences, each comprising a 50-mer single-stranded DNA fragment (synthesized by the P/AN Facility at Stanford University, Stanford, Calif.), representing the wild type and 3 mutant sequences of the CFTR gene. The fragments, termed WT (SEQ ID NO:2), ΔF508 (SEQ ID NO:3), MU1 (SEQ ID NO:4) and MU2 (SEQ ID NO:5) are presented in Table 1, below.

The presence of separated polynucleotides was detected using a UV-absorbance detector at the cathodic end.

Figure 1B:
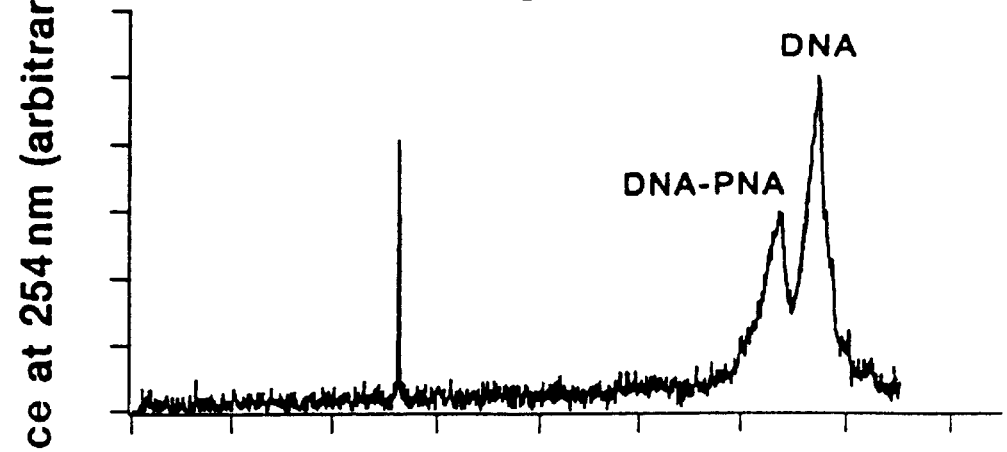
Figure 1C:
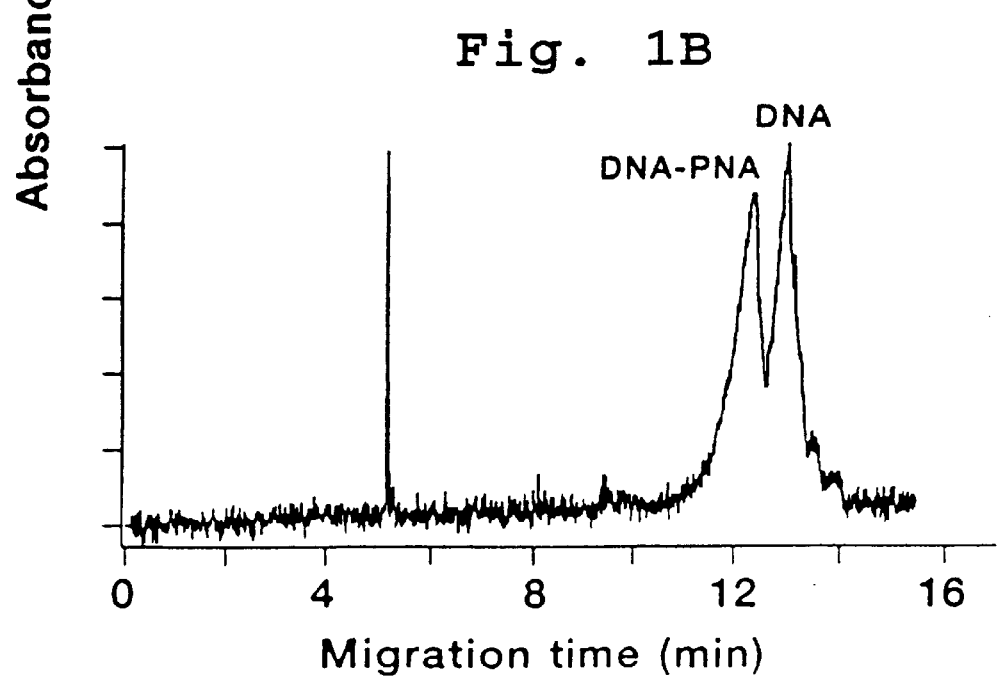

The results are shown in FIGS. 1A, 1B, 1C, 2A, 2B, 2C, 3A and 3B. FIGS. 1A, 1B and 1C show electropherograms of runs at 50° C. of the WT DNA fragment (SEQ ID NO:2) mixed with different amounts of the PNA probe. In the absence of PNA probe, only a peak corresponding to free (unhybridized) DNA was observed (FIG. 1A). FIG. 1B shows the resolution of a hybridization mixture containing 1 μl PNA probe (3.6 mM final concentration) and 450 μM WT fragment (SEQ ID NO:2). FIG. 1C shows an electropherogram of a mixture containing 5 mM PNA probe and 450 μM WT DNA fragment. Note that with the addition of PNA, a new peak with shorter migration time appeared, which grew at the expense of the peak at the longer migration time in the presence of higher concentrations of PNA. These data indicate that the peak at the shorter migration time corresponds to the PNA-DNA complex. Free PNA was not detected probably because it bound to the negatively charged fused-silica capillary wall. Similar electropherograms, but with a somewhat better separation, were obtained at lower temperatures.

Electrophoresis of a hybridization mixture containing the PNA probe (SEQ ID NO:1) and fragment ΔF508 (SEQ ID NO:3) resulted in only a single peak at 50° C., confirming that the deletion of three bases in this fragment lowers the denaturation temperature of the PNA-DNA hybrid to below 50° C. Two peaks were observed at 20° C., indicating that PNA can bind to the DNA in spite of the deletions at this lower temperature.

Figures 2A, 2B, 2C:
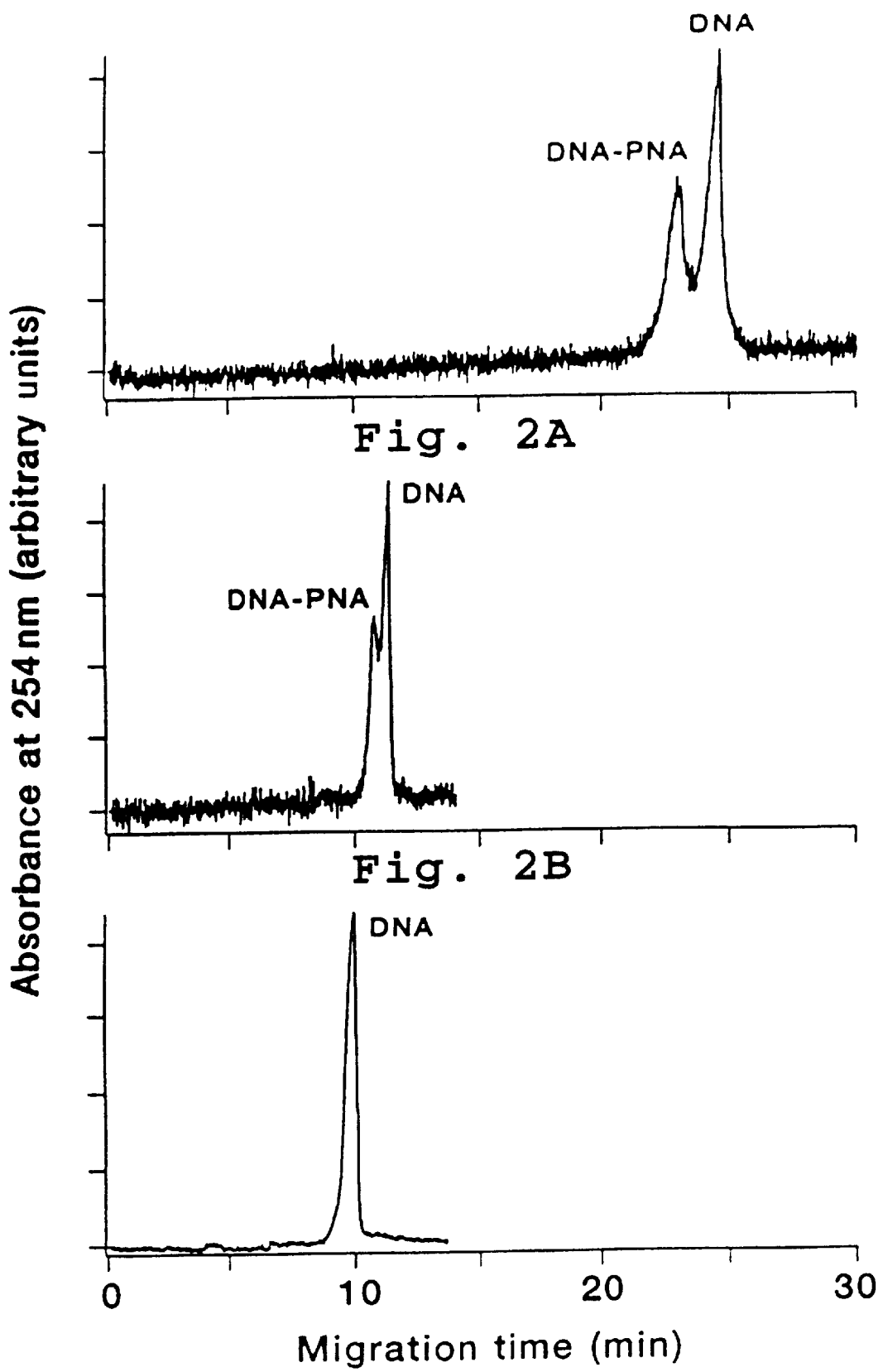
FIGS. 2A, 2B and 2C show free-solution electropherograms of a mixture of PNA probe and MU2 DNA (SEQ ID NO:5) run at 20° C.

FIGS. 2A, 2B and 2C shows similar results obtained with a hybridization mixture containing 5 mM PNA probe and 450 μM MU2 (SEQ ID NO:5). At 20° C. (FIG. 2A), both the MU2/DNA hybrid and free DNA peaks are clearly resolved.

TABLE 1

SYNTHETIC DNA FRAGMENTS OF THE CYSTIC FIBROSIS GENE

| DNA Fragment | Sequence | | | | | | Mutation | SEQ ID NO: |
|---|---|---|---|---|---|---|---|---|
| WT | 5'-{a}-A | TAT | CAT | CTT | TGG | TG-{b}-3' | none | 2 |
| ΔF508 | 5'-{a}-A | TAT | CAT | | TGG | TG-{b}-3' | deletion of three bases | 3 |
| MU1 | 5'-{a}-A | TAT | C<u>G</u>T | CTT | TGG | TG-{b}-3' | 1-base substitution (underlined) | 4 |
| MU2 | 5'-{a}-A | TAT | <u>AC</u>T | CTT | TGG | TG-{b}-3' | 2-base substitution (underlined) | 5 |

PNA Probe: H—CA CCA AAG ATG ATA T—Lys=NH$_2$ (SEQ ID NO: 1)
{a}: TGG CAC CAT TAA AGA AA (SEQ ID NO: 6)
{b}: T TTC cTA TGA TGA ATA TA (SEQ ID NO: 7)

The PNA probe and one of the 50-mer fragments were hybridized for 5–10 minutes at room temperature in 50 mM TBE, to allow for the formation of complexes between the PNA probe and target regions in the 50-mer fragments. Typical concentrations of DNA and PNA in the hybridization mixture were 5 mM and 450 μM bases, respectively.

The hybridization mixtures were then separated (to resolve complexed polynucleotides from non-complexed polynucleotides) either in the modified P/ACE Model 2000 (Beckman Instruments) capillary electrophoresis instrument described above (used for experiments run above 50° C.), or in a standard P/ACE Model 2000, which was also equipped with a 67-cm×75-mm inner diameter fused-silica capillary column (used for experiments run below 50° C.). The separations in both instruments were conducted using 50 mM TBE running buffer (recipe above) at a field strength of 210 V/cm.

At 50° C. (FIG. 2B) the two peaks had almost coalesced, and at 70° C. (FIG. 2C) only one peak, corresponding to the free DNA, was detected (FIG. 2C).

Figure 3A:
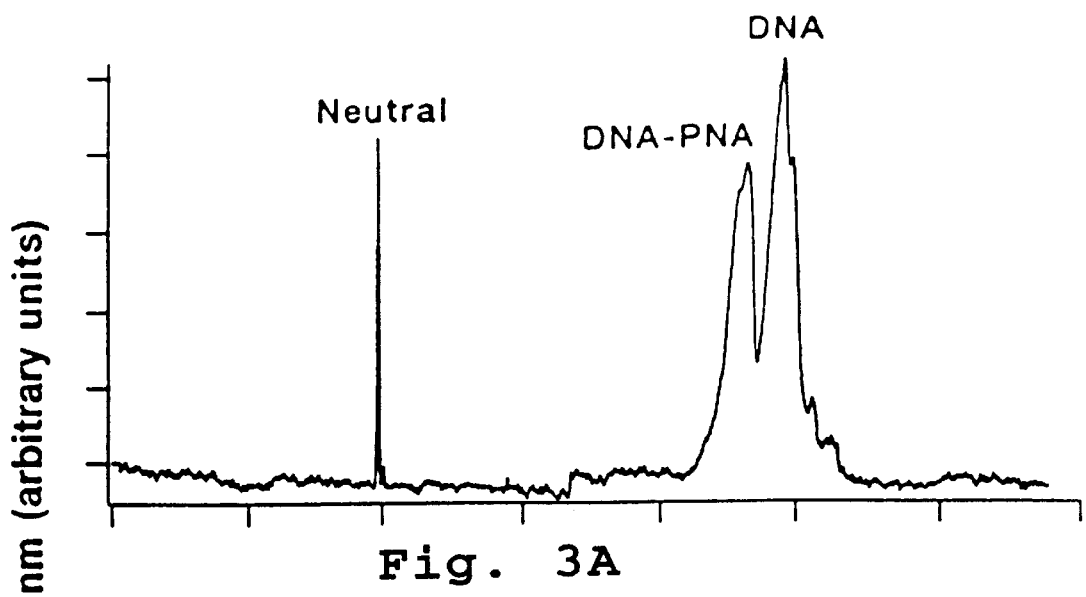
FIGS. 3A and 3B show a comparison of electropherograms at 70° C. of CF wild-type gene fragment (SEQ ID NO:2) hybridized with PNA probe (SEQ ID NO:1) (FIG. 3A) and MU1 DNA (SEQ ID NO:4) hybridized with PNA probe (FIG. 3B).
Figure 3B:
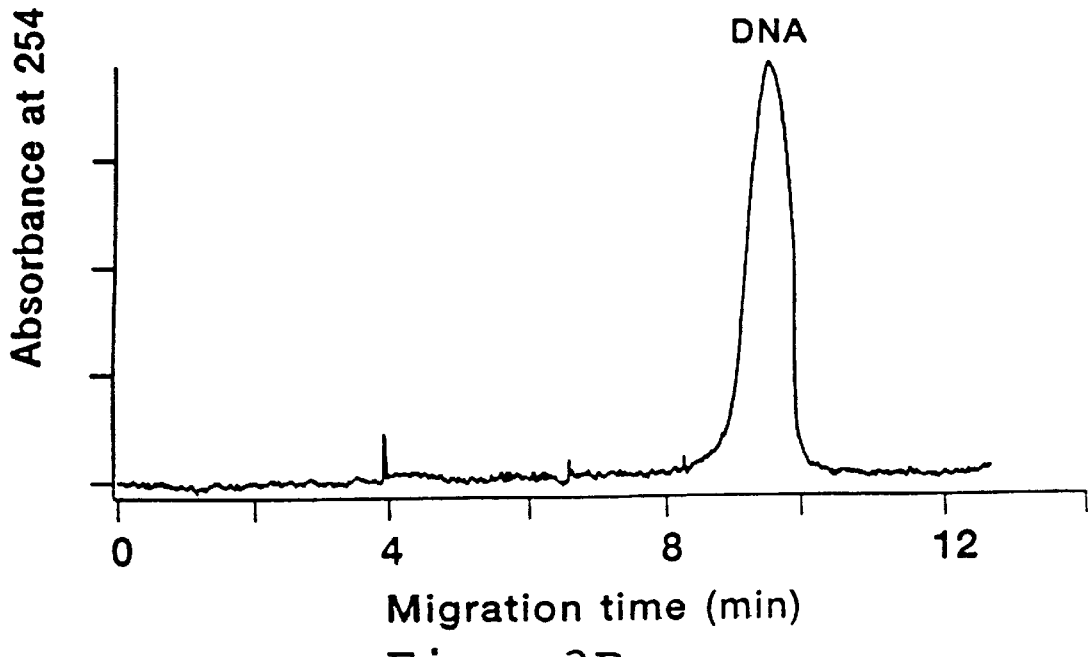

FIGS. 3A and 3B show experiments performed at 70° C. using hybridization solutions containing either WT fragment (SEQ ID NO:2) and PNA probe (SEQ ID NO:1) (FIG. 3A) or MU1 (SEQ ID NO:4) and PNA probe (SEQ ID NO:1). The data show that 70° C. is a suitable temperature for sequence discriminative binding, allowing binding of PNA to a fragment with a perfect match (WT) but not to a fragment with a single base substitution (MU1).

EXAMPLE 2

Detection of Mismatches in Double-stranded CFTR DNA Fragments Amplified from Human Genomic DNA Human genomic DNA was amplified using PCR from an individual having a normal CFTR gene and an individual homozygous for the cystic fibrosis ΔF508 mutation using standard methods (Mullis, 1987; Mullis, et al., 1987). The sequences of the amplification products are provided herein as SEQ ID NO:8 (normal (wild-type) individual) and SEQ ID NO:9 (individual with cystic fibrosis (ΔF508)).

The CF PNA probe described above (wild-type sequence; SEQ ID NO:1; 175 μM final concentration) was separately hybridized with each of the amplification products (final concentration 21 μM) at room temperature for 5–10 minutes and the mixtures were separated on the modified CE instrument at 50° C. as described in Example 1.

The results are shown in FIGS. 4A and 4B. The mixture containing amplification products from the normal individual contained perfectly-matched hybrids, consisting of the PNA probe (SEQ ID NO:1) hybridized to the wild-type fragment (SEQ ID NO:8), which were detected as a discrete peak in the FSCE (FIG. 4A). In contrast, no PNA/DNA hybrids were detected in the mixture containing the PNA probe (SEQ ID NO:1) and mutant (ΔF508) fragments (SEQ ID NO:9), indicating that such mismatched hybrids were not maintained at this temperature (50° C.).

These results indicate that methods of the present invention may be used to rapidly and reliably detect genetic mutations in PCR-amplified genomic DNA.

While the invention has been described with reference to specific methods and embodiments, it is appreciated that various modifications and changes may be made without departing from the invention.

It is claimed:

1. A method of detecting, in a sample containing a mixture of double stranded DNA polynucleotides, a target polynucleotide region having a sequence identical to a defined sequence, comprising
   reacting the sample with a peptide nucleic acid (PNA), having a sequence complementary to said defined sequence, under conditions that allow the formation of a complex between perfectly matched PNA and target-region sequences, but not between imperfectly matched PNA and target-region sequences having a single base pair mismatch, where said reacting includes contacting said sample with said PNA at about room temperature, and subsequently elevating the temperature of the reaction to between about 50° C. and about 80° C. to achieve conditions that allow the formation of complexes between perfectly matched PNA and target-region sequences, but not between said imperfectly matched PNA and target-region sequences
   separating complexed from non-complexed polynucleotides in the sample and
   detecting the presence of said complex,
   wherein said PNA is immobilized on a solid support, said reacting includes incubating the sample with the support, said separating includes washing said support to remove unbound polynucleotides, and said detecting includes detecting support-bound polynucleotides and adding labeled polycationic reporter.

2. A method of detecting, in a sample containing a mixture of polynucleotides, a target polynucleotide region having a sequence identical to a defined sequence, comprising
   reacting the sample with a peptide nucleic acid (PNA), having a sequence complementary to said defined sequence, under conditions that allow the formation of a complex between perfectly matched PNA and target-region sequences, but not between imperfectly matched PNA and target-region sequences,
   separating complexed from non-complexed polynucleotides in the sample by capillary electrophoresis, wherein said capillary electrophoresis instrument is a free-solution capillary electrophoresis instrument; and
   detecting the presence of said complex.

3. The method of claim 2, wherein said separating is carried out at a temperature between about 50° C. and 95° C.

4. The method of claim 3, wherein said separating is carried out at a temperature between about 50° C. and about 80° C.

5. The method of claim 2, wherein said detecting includes detecting using a UV-absorbance detector.

6. The method according to claim 2, wherein said PNA is at least 10 nucleotides in length.

7. The method of claim 6, wherein said PNA is not more than 15 nucleotides in length.

* * * * *

```
                            SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
         (A) LENGTH: 15 base pairs
         (B) TYPE: nucleic acid
         (C) STRANDEDNESS: single
         (D) TOPOLOGY: linear (ii) MOLECULE TYPE: DNA (iii) HYPOTHETICAL: NO (iv) ANTI-SENSE: NO (vi) ORIGINAL SOURCE:
         (C) INDIVIDUAL ISOLATE: PNA probe (ix) FEATURE:
         (A) NAME/KEY: misc_feature
         (B) LOCATION: 1..1
         (D) OTHER INFORMATION: /note= "H- at the 5' end of
             position 1 of the sequence"

(ix) FEATURE:
         (A) NAME/KEY: misc_feature
         (B) LOCATION: 15..15
         (D) OTHER INFORMATION: /note= "-Lys=NH2 at the 3' end of
             the sequence"

(xi) SEQUENCE DESCRIPTION: SEQ ID NO:1:

CACCAAAGAT GATAT                                                           15

(2) INFORMATION FOR SEQ ID NO:2:

(i) SEQUENCE CHARACTERISTICS:
         (A) LENGTH: 50 base pairs
         (B) TYPE: nucleic acid
         (C) STRANDEDNESS: single
         (D) TOPOLOGY: linear (ii) MOLECULE TYPE: DNA (iii) HYPOTHETICAL: NO (iv) ANTI-SENSE: NO (vi) ORIGINAL SOURCE:
         (C) INDIVIDUAL ISOLATE: WT fragment (Table 1)

(xi) SEQUENCE DESCRIPTION: SEQ ID NO:2:
```

```
TGGCACCATT AAAGAAAATA TCATCTTTGG TGTTTCCTAT GATGAATATA                50
```

(2) INFORMATION FOR SEQ ID NO:3:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: delta F 508 fragment (Table 1)

(xi) SEQUENCE DESCRIPTION: SEQ ID NO:3:

```
TGGCACCATT AAAGAAAATA TCATTGGTGT TTCCTATGAT GAATATA                   47
```

(2) INFORMATION FOR SEQ ID NO:4:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: MU1 fragment (Table 1)

(xi) SEQUENCE DESCRIPTION: SEQ ID NO:4:

```
TGGCACCATT AAAGAAAATA TCGTCTTTGG TGTTTCCTAT GATGAATATA                50
```

(2) INFORMATION FOR SEQ ID NO:5:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: MU2 fragment (Table 1)

(xi) SEQUENCE DESCRIPTION: SEQ ID NO:5:

```
TGGCACCATT AAAGAAAATA TACTCTTTGG TGTTTCCTAT GATGAATATA                50
```

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: common frag. sequence  (Table 1)

(xi) SEQUENCE DESCRIPTION: SEQ ID NO:6:

TGGCACCATT AAAGAAA                                                        17

(2) INFORMATION FOR SEQ ID NO:7:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: common frag. sequence  (Table 1)

(xi) SEQUENCE DESCRIPTION: SEQ ID NO:7:

TTTCCTATGA TGAATATA                                                       18

(2) INFORMATION FOR SEQ ID NO:8:

(i) SEQUENCE CHARACTERISTICS:
            (A) LENGTH: 143 base pairs
            (B) TYPE: nucleic acid
            (C) STRANDEDNESS: unknown
            (D) TOPOLOGY: unknown (ii) MOLECULE TYPE: cDNA to mRNA (iii) HYPOTHETICAL: NO (iv) ANTI-SENSE: NO (vi) ORIGINAL SOURCE:
            (C) INDIVIDUAL ISOLATE: CFTR 143-mer (xi) SEQUENCE DESCRIPTION: SEQ ID NO:8:

AAATTAAGCA CAGTGGAAGA ATTTCATTCT GTTCTCAGTT TTCCTGGATT ATGCCTGGCA         60

CCATTAAAGA AAATATCATC TTTGGTGTTT CCTATGATGA ATATAGATAC AGAAGCGTCA        120

TCAAAGCATG CCAACTAGAA GAG                                               143

(2) INFORMATION FOR SEQ ID NO:9:

(i) SEQUENCE CHARACTERISTICS:
            (A) LENGTH: 140 base pairs
            (B) TYPE: nucleic acid
            (C) STRANDEDNESS: unknown
            (D) TOPOLOGY: unknown (ii) MOLECULE TYPE: cDNA to mRNA (iii) HYPOTHETICAL: NO (iv) ANTI-SENSE: NO (vi) ORIGINAL SOURCE:
            (C) INDIVIDUAL ISOLATE: CFTR 140-mer -continued (xi) SEQUENCE DESCRIPTION: SEQ ID NO:9:

```
AAATTAAGCA CAGTGGAAGA ATTTCATTCT GTTCTCAGTT TTCCTGGATT ATGCCTGGCA        60

CCATTAAAGA AAATATCATT GGTGTTTCCT ATGATGAATA TAGATACAGA AGCGTCATCA       120

AAGCATGCCA ACTAGAAGAG                                                   140
```